United States Patent
Bailey et al.

(10) Patent No.: US 9,372,535 B2
(45) Date of Patent: Jun. 21, 2016

(54) SYSTEMS, ARTICLES, AND METHODS FOR ELECTROMYOGRAPHY-BASED HUMAN-ELECTRONICS INTERFACES

(71) Applicant: Thalmic Labs Inc., Kitchener (CA)

(72) Inventors: Matthew Bailey, Kitchener (CA); Stephen Lake, Kitchener (CA); Aaron Grant, Kitchener (CA)

(73) Assignee: THALMIC LABS INC., Kitchener (CA)

( * ) Notice: Subject to any disclaimer, the term of this patent is extended or adjusted under 35 U.S.C. 154(b) by 2 days.

(21) Appl. No.: 14/476,093

(22) Filed: Sep. 3, 2014

(65) Prior Publication Data

US 2015/0070270 A1    Mar. 12, 2015

Related U.S. Application Data

(60) Provisional application No. 61/874,846, filed on Sep. 6, 2013.

(51) Int. Cl.
*G06F 3/01* (2006.01)
*A61B 5/0488* (2006.01)
(Continued)

(52) U.S. Cl.
CPC ............... *G06F 3/015* (2013.01); *A61B 5/0488* (2013.01); *A61B 5/04888* (2013.01);
(Continued)

(58) Field of Classification Search
CPC .............. A61B 2505/09; A61B 2562/0219; A61B 5/0024; A61B 5/0488; A61B 5/04888; A61B 5/1123; A61B 5/6824; A61B 5/7278; G06F 3/015; G06F 3/017
USPC ........................................................ 345/156
See application file for complete search history.

(56) References Cited

U.S. PATENT DOCUMENTS 3,620,208 A   11/1971   Higley et al.
3,880,146 A    4/1975   Everett et al.
(Continued)

FOREIGN PATENT DOCUMENTS

EP    0 301 790 A2    2/1989
JP    2009-50679 A    3/2009
(Continued)

OTHER PUBLICATIONS

Costanza et al., "EMG as a Subtle Input Interface for Mobile Computing," Mobile HCI 2004, LNCS 3160, edited by S. Brewster and M. Dunlop, Springer-Verlag Berlin Heidelberg, pp. 426-430, 2004.

(Continued)

*Primary Examiner* — Quan-Zhen Wang
*Assistant Examiner* — Tony Davis
(74) *Attorney, Agent, or Firm* — Seed IP Law Group PLLC

(57) ABSTRACT

Human-electronics interfaces in which at least two wearable electromyography ("EMG") devices are operated to control virtually any electronic device are described. A first wearable EMG device is worn on a first part/location of a user's body and a second wearable EMG device is worn on a second part/location of the user's body. Muscle activity is detected by the two wearable EMG devices and corresponding communication signals are transmitted to an electronic device to control functions thereof. The two wearable EMG devices may communicate with one another. This configuration enables a user to perform elaborate gestures having multiple components (e.g., "two-arm" gestures) with each wearable EMG device detecting a different component, as well as separate gestures (e.g., separate "one-arm" gestures) individually detected and processed by each wearable EMG device.

19 Claims, 3 Drawing Sheets

(51) Int. Cl.
*A61B 5/11* (2006.01)
*A61B 5/00* (2006.01)

(52) U.S. Cl.
CPC ............ *A61B 5/1123* (2013.01); *A61B 5/6824* (2013.01); *G06F 3/017* (2013.01); *A61B 5/0024* (2013.01); *A61B 5/7278* (2013.01); *A61B 2505/09* (2013.01); *A61B 2562/0219* (2013.01)

(56) References Cited

U.S. PATENT DOCUMENTS

| | | | |
|---|---|---|---|
| 4,602,639 | A | 7/1986 | Hoogendoorn et al. |
| 5,003,978 | A | 4/1991 | Dunseath, Jr. |
| 5,482,051 | A | 1/1996 | Reddy et al. |
| 5,683,404 | A | 11/1997 | Johnson |
| 6,032,530 | A | 3/2000 | Hock |
| 6,238,338 | B1 | 5/2001 | DeLuca et al. |
| 6,244,873 | B1 | 6/2001 | Hill et al. |
| 6,487,906 | B1 | 12/2002 | Hock |
| 6,510,333 | B1 | 1/2003 | Licata et al. |
| 6,720,984 | B1 | 4/2004 | Jorgensen et al. |
| 6,807,438 | B1 | 10/2004 | Brun Del Re et al. |
| 6,865,409 | B2 | 3/2005 | Getsla et al. |
| 6,965,842 | B2 | 11/2005 | Rekimoto |
| 7,173,437 | B2 | 2/2007 | Hervieux et al. |
| 7,333,090 | B2 | 2/2008 | Tanaka et al. |
| 7,596,393 | B2 | 9/2009 | Jung et al. |
| 7,809,435 | B1* | 10/2010 | Ettare .................. A61B 5/0002 600/546 |
| 8,054,061 | B2 | 11/2011 | Prance et al. |
| 8,170,656 | B2 | 5/2012 | Tan et al. |
| 8,421,634 | B2* | 4/2013 | Tan .......................... G06F 1/163 340/573.1 |
| 8,447,704 | B2 | 5/2013 | Tan et al. |
| 8,922,481 | B1 | 12/2014 | Kauffmann et al. |
| 2002/0032386 | A1 | 3/2002 | Sackner et al. |
| 2002/0077534 | A1 | 6/2002 | DuRousseau |
| 2003/0036691 | A1 | 2/2003 | Stanaland et al. |
| 2004/0068409 | A1 | 4/2004 | Tanaka et al. |
| 2004/0073104 | A1 | 4/2004 | Brun del Re et al. |
| 2004/0210165 | A1 | 10/2004 | Marmaropoulos et al. |
| 2005/0119701 | A1 | 6/2005 | Lauter et al. |
| 2005/0177038 | A1 | 8/2005 | Kolpin et al. |
| 2006/0061544 | A1* | 3/2006 | Min .................... G02B 27/0093 345/156 |
| 2006/0121958 | A1* | 6/2006 | Jung ........................ G06F 3/015 455/575.1 |
| 2008/0136775 | A1* | 6/2008 | Conant .................. G06F 3/017 345/156 |
| 2009/0051544 | A1* | 2/2009 | Niknejad ................ G06F 3/011 340/573.1 |
| 2009/0251407 | A1* | 10/2009 | Flake ...................... G06F 3/014 345/156 |
| 2009/0318785 | A1* | 12/2009 | Ishikawa ............ A61B 5/14553 600/310 |
| 2009/0326406 | A1* | 12/2009 | Tan .......................... G06F 1/163 600/546 |
| 2009/0327171 | A1* | 12/2009 | Tan ........................ G06F 3/015 706/12 |
| 2010/0041974 | A1 | 2/2010 | Ting et al. |
| 2010/0280628 | A1 | 11/2010 | Sankai |
| 2010/0293115 | A1 | 11/2010 | Seyed Momen |
| 2010/0317958 | A1 | 12/2010 | Beck et al. |
| 2011/0133934 | A1* | 6/2011 | Tan .......................... G06F 1/163 340/573.1 |
| 2011/0134026 | A1* | 6/2011 | Kang ...................... G06F 3/011 345/156 |
| 2011/0166434 | A1 | 7/2011 | Gargiulo |
| 2011/0172503 | A1* | 7/2011 | Knepper ............ A61B 5/02055 600/301 |
| 2012/0029322 | A1* | 2/2012 | Wartena ............... A61B 5/0476 600/301 |
| 2012/0101357 | A1 | 4/2012 | Hoskuldsson et al. |
| 2012/0157789 | A1 | 6/2012 | Kangas et al. |
| 2012/0165695 | A1* | 6/2012 | Kidmose ............. A61B 5/0476 600/545 |
| 2012/0188158 | A1* | 7/2012 | Tan ....................... A61B 5/0488 345/156 |
| 2012/0209134 | A1 | 8/2012 | Morita et al. |
| 2012/0265090 | A1* | 10/2012 | Fink ....................... A61B 5/4343 600/546 |
| 2012/0302858 | A1* | 11/2012 | Kidmose ............. A61B 5/0476 600/379 |
| 2013/0005303 | A1* | 1/2013 | Song .................. A61B 5/02438 455/411 |
| 2013/0027341 | A1 | 1/2013 | Mastandrea |
| 2013/0127708 | A1* | 5/2013 | Jung .................... A61B 5/0006 345/156 |
| 2013/0165813 | A1 | 6/2013 | Chang et al. |
| 2013/0191741 | A1 | 7/2013 | Dickinson et al. |
| 2013/0198694 | A1 | 8/2013 | Rahman et al. |
| 2013/0317648 | A1 | 11/2013 | Assad |
| 2014/0028546 | A1* | 1/2014 | Jeon ........................ G06F 3/014 345/156 |
| 2014/0049417 | A1* | 2/2014 | Abdurrahman ........ G08C 19/00 341/176 |
| 2014/0349257 | A1* | 11/2014 | Connor .............. G09B 19/0092 434/127 |
| 2014/0354528 | A1* | 12/2014 | Laughlin ................. G06F 3/011 345/156 |
| 2014/0354529 | A1* | 12/2014 | Laughlin ................. G06F 3/017 345/156 |

FOREIGN PATENT DOCUMENTS

| | | |
|---|---|---|
| KR | 20120094870 A | 8/2012 |
| KR | 20120097997 A | 9/2012 |
| WO | 2011/070554 A2 | 6/2011 |

OTHER PUBLICATIONS

Costanza et al., "Toward Subtle Intimate Interfaces for Mobile Devices Using an EMG Controller," CHI 2005, Proceedings of the SIGCHI Conference on Human Factors in Computing Systems, pp. 481-489, 2005.

Ghasemzadeh et al., "A Body Sensor Network With Electromyogram and Inertial Sensors: Multimodal Interpretation of Muscular Activities," IEEE Transactions on Information Technology in Biomedicine, vol. 14, No. 2, pp. 198-206, Mar. 2010.

Gourmelon et al., "Contactless sensors for Surface Electromyography," Proceedings of the 28th IEEE EMBS Annual International Conference, New York City, NY, Aug. 30-Sep. 3, 2006, pp. 2514-2517.

International Search Report and Written Opinion, mailed May 16, 2014, for corresponding International Application No. PCT/US2014/017799, 9 pages.

International Search Report and Written Opinion, mailed Aug. 21, 2014, for corresponding International Application No. PCT/US2014/037863, 10 pages.

International Search Report and Written Opinion, mailed Nov. 21, 2014, for corresponding International Application No. PCT/US2014/052143, 9 pages.

International Search Report and Written Opinion, mailed Feb. 27, 2015, for corresponding International Application No. PCT/US2014/067443, 10 pages.

International Search Report and Written Opinion, mailed May 27, 2015, for corresponding International Application No. PCT/US2015/015675, 9 pages.

Morris et al., "Emerging Input Technologies for Always-Available Mobile Interaction," *Foundations and Trends in Human-Computer Interaction* 4(4):245-316, 2010. (74 total pages).

Naik et al., "Real-Time Hand Gesture Identification for Human Computer Interaction Based on ICA of Surface Electromyogram," IADIS International Conference Interfaces and Human Computer Interaction 2007, 8 pages.

Picard et al., "Affective Wearables," Proceedings of the IEEE 1st International Symposium on Wearable Computers, ISWC, Cambridge, MA, USA, Oct. 13-14, 1997, pp. 90-97.

(56) References Cited

OTHER PUBLICATIONS

Rekimoto, "GestureWrist and GesturePad: Unobtrusive Wearable Interaction Devices," ISWC '01 Proceedings of the $5^{th}$ IEEE International Symposium on Wearable Computers, 2001, 7 pages.

Saponas et al., "Making Muscle-Computer Interfaces More Practical," CHI 2010, Atlanta, Georgia, USA, Apr. 10-15, 2010, 4 pages.

Sato et al., "Touche. Enhancing Touch Interaction on Humans, Screens, Liquids, and Everyday Objects," CHI' 12, May 5-10, 2012, Austin, Texas.

Ueno et al., "A Capacitive Sensor System for Measuring Laplacian Electromyogram through Cloth: A Pilot Study," Proceedings of the $29^{th}$ Annual International Conference of the IEEE EMBS, Cite Internationale, Lyon, France, Aug. 23-26, 2007.

Ueno et al., "Feasibility of Capacitive Sensing of Surface Electromyographic Potential through Cloth," *Sensors and Materials* 24(6):335-346, 2012.

Xiong et al., "A Novel HCI based on EMG and IMU," Proceedings of the 2011 IEEE International Conference on Robotics and Biomimetics, Phuket, Thailand, Dec. 7-11, 2011, 5 pages.

Zhang et al., "A Framework for Hand Gesture Recognition Based on Accelerometer and EMG Sensors," IEEE Transactions on Systems, Man, and Cybernetics—Part A: Systems and Humans, vol. 41, No. 6, pp. 1064-1076, Nov. 2011.

\* cited by examiner

SYSTEMS, ARTICLES, AND METHODS FOR ELECTROMYOGRAPHY-BASED HUMAN-ELECTRONICS INTERFACES

BACKGROUND

1. Technical Field

The present systems, articles, and methods generally relate to human-electronics interfaces that provide electromyographic control of electronic devices, and particularly relate to human-electronics interfaces that employ multiple wearable electromyography devices.

2. Description of the Related Art

Wearable Electronic Devices

Electronic devices are commonplace throughout most of the world today. Advancements in integrated circuit technology have enabled the development of electronic devices that are sufficiently small and lightweight to be carried by the user. Such "portable" electronic devices may include on-board power supplies (such as batteries or other power storage systems) and may be designed to operate without any wire-connections to other electronic systems; however, a small and lightweight electronic device may still be considered portable even if it includes a wire-connection to another electronic system. For example, a microphone may be considered a portable electronic device whether it is operated wirelessly or through a wire-connection.

The convenience afforded by the portability of electronic devices has fostered a huge industry. Smartphones, audio players, laptop computers, tablet computers, and ebook readers are all examples of portable electronic devices. However, the convenience of being able to carry a portable electronic device has also introduced the inconvenience of having one's hand(s) encumbered by the device itself. This problem is addressed by making an electronic device not only portable, but wearable.

A wearable electronic device is any portable electronic device that a user can carry without physically grasping, clutching, or otherwise holding onto the device with their hands. For example, a wearable electronic device may be attached or coupled to the user by a strap or straps, a band or bands, a clip or clips, an adhesive, a pin and clasp, an article of clothing, tension or elastic support, an interference fit, an ergonomic form, etc. Examples of wearable electronic devices include digital wristwatches, electronic armbands, electronic rings, electronic ankle-bracelets or "anklets," head-mounted electronic display units, hearing aids, and so on.

Human-Electronics Interfaces

A wearable electronic device may provide direct functionality for a user (such as audio playback, data display, computing functions, etc.) or it may provide electronics to interact with, receive information from, or control another electronic device. For example, a wearable electronic device may include sensors that detect inputs effected by a user and transmit signals to another electronic device based on those inputs. Sensor-types and input-types may each take on a variety of forms, including but not limited to: tactile sensors (e.g., buttons, switches, touchpads, or keys) providing manual control, acoustic sensors providing voice-control, electromyography sensors providing gesture control, and/or accelerometers providing gesture control.

A human-computer interface ("HCI") is an example of a human-electronics interface. The present systems, articles, and methods may be applied to HCIs, but may also be applied to any other form of human-electronics interface.

Electromyography Devices

Electromyography ("EMG") is a process for detecting and processing the electrical signals generated by muscle activity. EMG devices employ EMG sensors that are responsive to the range of electrical potentials (typically μV-mV) involved in muscle activity. EMG signals may be used in a wide variety of applications, including: medical monitoring and diagnosis, muscle rehabilitation, exercise and training, prosthetic control, and even in controlling functions of electronic devices.

Human-electronics interfaces that employ EMG have been proposed in the art. For example, U.S. Pat. Nos. 6,244,873 and 8,170,656 describe such systems. Characteristics that are common to these known proposals will now be described.

Typically, such systems (including the two examples listed above) employ a single processor-based wearable EMG device (meaning that the wearable EMG device itself includes at least one on-board processor) that is worn at a single location on a user's body (e.g., on one of a user's arms). The single wearable EMG device detects muscle activity at that single location and outputs signals based on the detected muscle activity. In this way, a user may perform physical gestures to control functions of an electronic device; however, the set of gestures that the user can perform is limited to gestures that involve only the single location of the user's body at which the EMG device is worn. While common to typical EMG-based human-electronics interfaces proposed in the art, this limitation is disadvantageous for at least two reasons: i) it unduly restricts the library of gestures available to the user, and thereby restricts the number of functions that the user can control, and ii) it limits the intuitiveness of the interface because it imposes an unnatural one-sidedness on the user's gestures. There is a need in the art for EMG-based human-electronics interfaces that enable a wider variety of gestures and better-promote the user's natural and intuitive body movements.

BRIEF SUMMARY

A first wearable electromyography ("EMG") device for use in conjunction with a second wearable EMG device to control an electronic device may be summarized as including: at least one EMG sensor responsive to muscle activity of a user of the first wearable EMG device and provide at least one signal in response to the detected muscle activity; a processor communicatively coupled to the at least one EMG sensor, the processor to in use process the at least one signal provided by the at least one EMG sensor; at least one communication terminal communicatively coupled to the processor, the at least one communication terminal to in use send communication signals to both the electronic device and the second wearable EMG device and to receive communication signals from at least the second wearable EMG device; and a non-transitory processor-readable storage medium communicatively coupled to the processor, wherein the non-transitory processor-readable storage medium stores: processor-executable EMG processing instructions that, when executed by the processor, cause the processor to process the at least one signal provided by the at least one EMG sensor, first processor-executable communication instructions that, when executed by the processor, cause the processor to communicate with the electronic device, and second processor-executable communication instructions that, when executed by the processor, cause the processor to communicate with the second wearable EMG device. The first wearable EMG device may further include at least one accelerometer communicatively coupled to the processor, the at least one accelerometer responsive to motion effected by the user of the first wearable EMG device and provide at least one signal in response to the detected motion, and wherein the non-transitory processor-readable storage medium further stores processor-executable motion processing instructions that, when executed by the processor, cause the processor to process the at least one signal provided by the at least one accelerometer.

The processor may be selected from the group consisting of: a digital microprocessor, a digital microcontroller, a digital signal processor, a graphics processing unit, an application specific integrated circuit, a programmable gate array, and a programmable logic unit. The at least one EMG sensor may include a plurality of EMG sensors, and the first wearable EMG device may include a set of communicative pathways communicatively coupled to route signals provided by the plurality of EMG sensors to the processor, wherein each EMG sensor in the plurality of EMG sensors is communicatively coupled to the processor by at least one communicative pathway from the set of communicative pathways. The first wearable EMG device may further include a set of pod structures that form physically coupled links of the first wearable EMG device, wherein each pod structure in the set of pod structures is positioned adjacent and physically coupled to at least one other pod structure in the set of pod structures, and wherein the set of pod structures comprises at least two sensor pods and a processor pod, each of the at least two sensor pods comprising a respective EMG sensor from the plurality of EMG sensors and the processor pod comprising the processor. Each pod structure in the set of pod structures may be positioned adjacent and in between two other pod structures in the set of pod structures and physically coupled to the two other pod structures in the set of pod structures, and the set of pod structures may form a perimeter of an annular configuration. The first wearable EMG device may include at least one adaptive coupler, wherein each respective pod structure in the set of pod structures is adaptively physically coupled to at least one adjacent pod structure in the set of pod structures by at least one adaptive coupler.

The at least one communication terminal may include at least one of a wireless communication terminal and/or a tethered connector port. The at least one communication terminal may include a first communication terminal to in use send communication signals to the electronic device, and a second communication terminal to in use send communication signals to the second wearable EMG device and receive communication signals from the second wearable EMG device.

A system that enables electromyographic control of an electronic device may be summarized as including: a first wearable electromyography ("EMG") device comprising: at least a first EMG sensor responsive to muscle activity of a user of the first wearable EMG device and provide at least one signal in response to the detected muscle activity, a first processor communicatively coupled to the at least a first EMG sensor, the first processor to in use process the at least one signal provided by the at least a first EMG sensor, and a first communication terminal communicatively coupled to the first processor, the first communication terminal to in use transmit communication signals from the first wearable EMG device; a second wearable EMG device comprising: at least a second EMG sensor responsive to muscle activity of a user of the second wearable EMG device and provide at least one signal in response to the detected muscle activity, a second processor communicatively coupled to the at least a second EMG sensor, the second processor to in use process the at least one signal provided by the at least a second EMG sensor, and a second communication terminal communicatively coupled to the second processor, the second communication terminal to in use transmit communication signals from the second wearable EMG device; and an electronic device comprising: a third communication terminal to in use receive communication signals from at least one of the first wearable EMG device and the second wearable EMG device, and a third processor communicatively coupled to the third communication terminal, the third processor to in use effect functions of the electronic device based on the communication signals received by the third communication terminal. The first wearable EMG device may include a first non-transitory processor-readable storage medium communicatively coupled to the first processor, wherein the first non-transitory processor-readable storage medium stores first processor-executable EMG processing instructions that, when executed by the first processor, cause the first processor to process at least one signal provided by the at least a first EMG sensor. The second wearable EMG device may include a second non-transitory processor-readable storage medium communicatively coupled to the second processor, wherein the second non-transitory processor-readable storage medium stores second processor-executable EMG processing instructions that, when executed by the second processor, cause the second processor to process at least one signal provided by the at least a second EMG sensor.

At least one of the first communication terminal of the first wearable EMG device and the second communication terminal of the second wearable EMG device may be receptive of communication signals from the other one of the second communication terminal of the second wearable EMG device and the first communication terminal of the first wearable EMG device. The first wearable EMG device may include a first non-transitory processor-readable storage medium communicatively coupled to the first processor, wherein the first non-transitory processor-readable storage medium stores first processor-executable communication instructions that, when executed by the first processor, cause the first processor to communicate with the second wearable EMG device; and the second wearable EMG device may include a second non-transitory processor-readable storage medium communicatively coupled to the second processor, wherein the second non-transitory processor-readable storage medium stores second processor-executable communication instructions that, when executed by the second processor, cause the second processor to communicate with the first wearable EMG device.

The first wearable EMG device may include at least a first accelerometer communicatively coupled to the first processor, the at least a first accelerometer responsive to motion effected by the user of the first wearable EMG device and provide at least one signal in response to the detected motion. The second wearable EMG device may include at least a second accelerometer communicatively coupled to the second processor, the at least a second accelerometer responsive to motion effected by the user of the second wearable EMG device and provide at least one signal in response to the detected motion. The first wearable EMG device may include a first non-transitory processor-readable storage medium communicatively coupled to the first processor, wherein the first non-transitory processor-readable storage medium stores first processor-executable motion instructions that, when executed by the first processor, cause the first processor to process the at least one signal provided by the at least a first accelerometer; and the second wearable EMG device may include a second non-transitory processor-readable storage medium communicatively coupled to the second processor, wherein the second non-transitory processor-readable storage medium stores second processor-executable motion instructions that, when executed by the second processor, cause the second processor to process the at least one signal provided by the at least a second accelerometer.

The electronic device may include a non-transitory processor-readable storage medium communicatively coupled to the third processor, wherein the non-transitory processor-readable storage medium stores processor-executable instructions that, when executed by the third processor, cause the third processor to effect functions of the electronic device based at least in part on the communication signals received by the third communication terminal.

The first communication terminal, the second communication terminal, and the third communication terminal may each include a respective wireless communication terminal. The electronic device may be selected from the group consisting of: a computer, a laptop computer, a tablet computer, a mobile phone, a smartphone, a portable electronic device, an audio player, a television, a video player, a video game console, a robot, a light switch, and a vehicle.

A method of using at least one gesture of a user to electromyographically control an electronic device may be summarized as including: detecting muscle activity corresponding to at least one gesture of the user by a first wearable electromyography ("EMG") device; detecting muscle activity corresponding to at least one gesture of the user by a second wearable EMG device; transmitting at least a first signal to the electronic device from at least one of the first wearable EMG device and/or the second wearable EMG device, wherein the at least a first signal is based at least in part on the muscle activity detected by the first wearable EMG device and the muscle activity detected by the second wearable EMG device; receiving the at least a first signal by the electronic device; processing the at least a first signal by the electronic device; and performing at least one function by the electronic device based at least in part on the processing the at least a first signal.

Detecting muscle activity corresponding to at least one gesture of the user by a first wearable EMG device may include detecting muscle activity corresponding to a first gesture of the user by the first wearable EMG device; and detecting muscle activity corresponding to at least one gesture of the user by a second wearable EMG device may include detecting muscle activity corresponding to the first gesture of the user by the second wearable EMG device.

Detecting muscle activity corresponding to at least one gesture of the user by a first wearable EMG device may include detecting muscle activity corresponding to a first gesture of the user by the first wearable EMG device; and detecting muscle activity corresponding to at least one gesture of the user by a second wearable EMG device may include detecting muscle activity corresponding to a second gesture of the user by the second wearable EMG device.

The first wearable EMG device may be worn on a first arm of the user and the second wearable EMG device may be worn on a second arm of the user.

Transmitting at least a first signal to the electronic device from at least one of the first wearable EMG device and/or the second wearable EMG device may include transmitting a first signal to the electronic device from the first wearable EMG device and transmitting a second signal to the electronic device from the second wearable EMG device, and the first signal may be based at least in part on the muscle activity detected by the first wearable EMG device and the second signal is based at least in part on the muscle activity detected by the second wearable EMG device.

Transmitting at least a first signal to the electronic device from at least one of the first wearable EMG device and/or the second wearable EMG device may include transmitting a first signal from the first wearable EMG device to the second wearable EMG device and transmitting at least a second signal from the second wearable EMG device to the electronic device, and the first signal may be based at least in part on the muscle activity detected by the first wearable EMG device and the at least a second signal is based at least in part on both the muscle activity detected by the first wearable EMG device and the muscle activity detected by the second wearable EMG device.

The method may further include transmitting at least a second signal from the first wearable EMG device to the second wearable EMG device. The method may further include transmitting at least a third signal from the second wearable EMG device to the first wearable EMG device.

The method may further include detecting motion corresponding to at least one gesture of the user by the first wearable EMG device, wherein the at least a first signal is based at least in part on the motion detected by the first wearable EMG device. The method may further include detecting motion corresponding to at least one gesture of the user by the second wearable EMG device, wherein the at least a first signal is based at least in part on the motion detected by the second wearable EMG device.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

Figure 1:
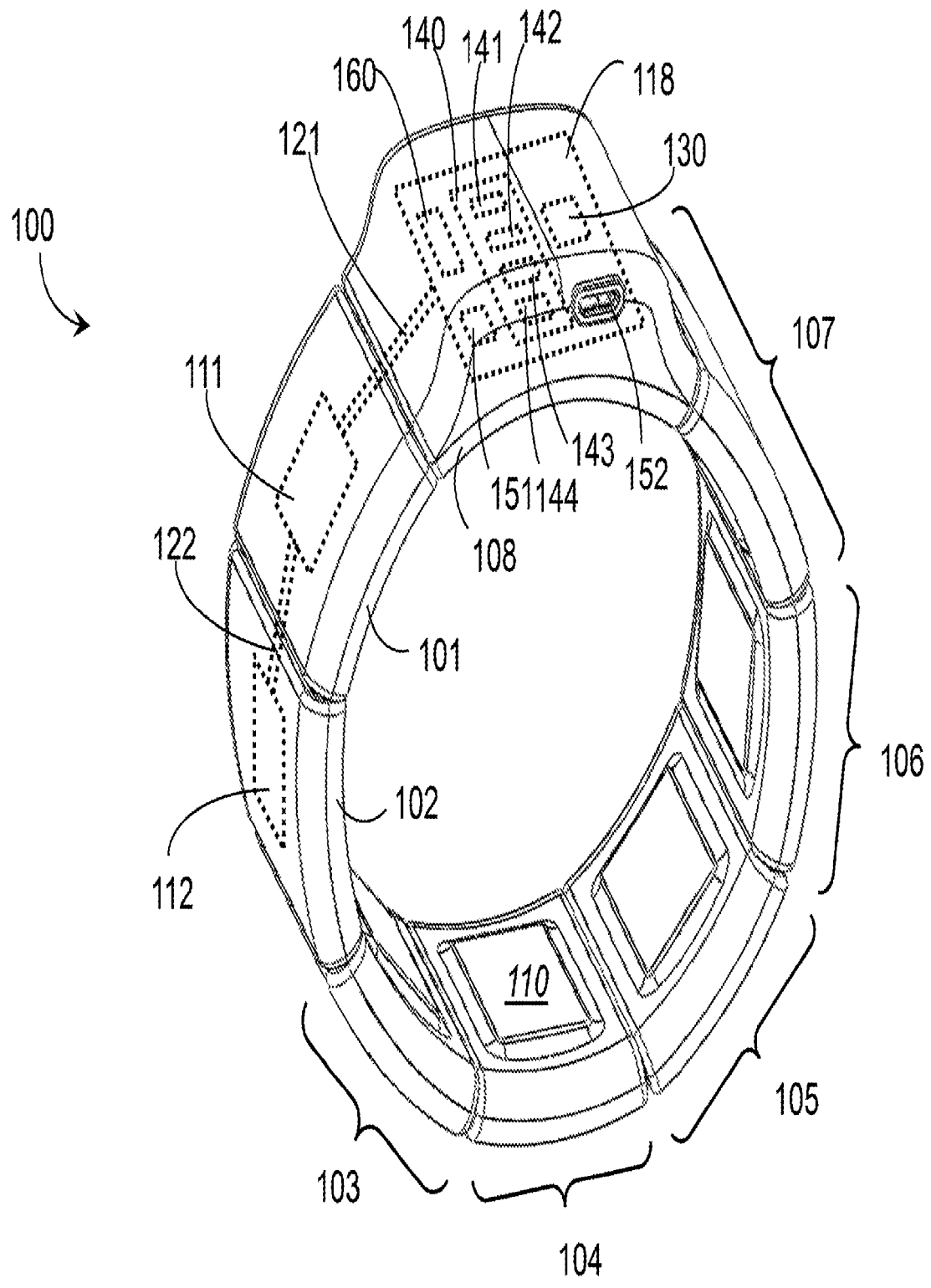
FIG. 1 is a perspective view of an exemplary first wearable EMG device for use in conjunction with a second wearable EMG device to control an electronic device in accordance with the present systems, articles, and methods.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with electronic devices, and in particular portable electronic devices such as wearable electronic devices, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

The various embodiments described herein provide systems, articles, and methods for human-electronics interfaces that enable a wide variety of natural and intuitive user gestures. The human-electronics interfaces described herein employ at least two wearable EMG devices that are worn at different locations on the user's body. Signals are output from the at least two wearable EMG devices based on gestures performed by the user, and the signals are used to control functions of another electronic device.

Throughout this specification and the appended claims, the term "gesture" is used to generally refer to a physical action (e.g., a movement, a stretch, a flex, a pose, etc.) performed or otherwise effected by a user. Any physical action performed or otherwise effected by a user that involves detectable muscle activity (detectable, e.g., by at least one appropriately positioned EMG sensor) and/or detectable motion (detectable, e.g., by at least one appropriately positioned accelerometer) may constitute a gesture in the present systems, articles, and methods.

Furthermore, throughout this specification and the appended claims, the terms "part" and "location" are often used in the context of a user's body, as in "a part/location of a user's body." Unless the specific context requires otherwise, throughout this specification and the appended claims, two distinct "parts" of a user's body are any two areas or regions of the user's body that can readily be moved in relation to one another (e.g., two arms, an arm and a leg, a lower arm and an upper arm, a hand and a torso, etc.), and two distinct "locations" of a user's body are any two areas or regions of the user's body that are spatially separated from one another by at least 5 centimeters in a non-circumferential direction (e.g., spatially separated by at least 5 centimeters along a length of the user's arm).

FIG. 1 is a perspective view of an exemplary first wearable EMG device 100 for use in conjunction with a second wearable EMG device (not shown) to control an electronic device (not shown) in accordance with the present systems, articles, and methods. In other words, exemplary first wearable EMG device 100 forms part of a human-electronics interface that comprises at least two wearable EMG devices. Exemplary first wearable EMG device 100 is an armband designed to be worn on the wrist, forearm, or upper arm of a user, though a person of skill in the art will appreciate that the teachings described herein may readily be applied in wearable EMG devices designed to be worn elsewhere on the body of the user (such as on the leg, ankle, finger, foot, torso, or neck of the user). Some details of various implementations of exemplary first wearable EMG device 100 are described in at least U.S. Provisional Patent Application Ser. No. 61/752,226 (now U.S. Non-Provisional patent application Ser. No. 14/155, 107), U.S. Provisional Patent Application Ser. No. 61/768, 322 (now U.S. Non-Provisional patent application Ser. No. 14/186,889), U.S. Provisional Patent Application Ser. No. 61/771,500 (now U.S. Non-Provisional patent application Ser. No. 14/194,252), U.S. Provisional Patent Application Ser. No. 61/869,526 (now U.S. Non-Provisional patent application Ser. No. 14/465,194), and U.S. Provisional Patent Application Ser. No. 61/872,569, each of which is incorporated herein by reference in its entirety.

Device 100 includes a set of eight pod structures 101, 102, 103, 104, 105, 106, 107, and 108 that form physically coupled links of the first wearable EMG device 100. Each pod structure in the set of eight pod structures 101, 102, 103, 104, 105, 106, 107, and 108 is positioned adjacent and in between two other pod structures in the set of eight pod structures and the set of pod structures forms a perimeter of an annular or closed loop configuration. For example, pod structure 101 is positioned adjacent and in between pod structures 102 and 108 at least approximately on a perimeter of the annular or closed loop configuration of pod structures, pod structure 102 is positioned adjacent and in between pod structures 101 and 103 at least approximately on the perimeter of the annular or closed loop configuration, pod structure 103 is positioned adjacent and in between pod structures 102 and 104 at least approximately on the perimeter of the annular or closed loop configuration, and so on. Each of pod structures 101, 102, 103, 104, 105, 106, 107, and 108 is physically coupled to the two adjacent pod structures by at least one adaptive coupler (not visible in FIG. 1). For example, pod structure 101 is physically coupled to pod structure 108 by an adaptive coupler and to pod structure 102 by an adaptive coupler. The term "adaptive coupler" is used throughout this specification and the appended claims to denote a system, article or device that provides flexible, adjustable, modifiable, extendable, extensible, or otherwise "adaptive" physical coupling. Adaptive coupling is physical coupling between two objects that permits limited motion of the two objects relative to one another. An example of an adaptive coupler is an elastic material such as an elastic band. Thus, each of pod structures 101, 102, 103, 104, 105, 106, 107, and 108 in the set of eight pod structures may be adaptively physically coupled to the two adjacent pod structures by at least one elastic band. The set of eight pod structures may be physically bound in the annular or closed loop configuration by a single elastic band that couples over or through all pod structures or by multiple separate elastic bands that couple between adjacent pairs of pod structures or between groups of adjacent pairs of pod structures. Device 100 is depicted in FIG. 1 with the at least one adaptive coupler completely retracted and contained within the eight pod structures 101, 102, 103, 104, 105, 106, 107, and 108 (and therefore the at least one adaptive coupler is not visible in FIG. 1). Further details of adaptive coupling in wearable electronic devices are described in, for example, U.S. Provisional Application Ser. No. 61/860,063 (now U.S. Non-Provisional patent application Ser. No. 14/276,575), which is incorporated herein by reference in its entirety.

Throughout this specification and the appended claims, the term "pod structure" is used to refer to an individual link, segment, pod, section, structure, component, etc. of a wearable EMG device. For the purposes of the present systems, articles, and methods, an "individual link, segment, pod, section, structure, component, etc." (i.e., a "pod structure") of a wearable EMG device is characterized by its ability to be moved or displaced relative to another link, segment, pod, section, structure component, etc. of the wearable EMG device. For example, pod structures 101 and 102 of device 100 can each be moved or displaced relative to one another within the constraints imposed by the adaptive coupler providing adaptive physical coupling therebetween. The desire for pod structures 101 and 102 to be movable/displaceable relative to one another specifically arises because device 100 is a wearable EMG device that advantageously accommodates the movements of a user and/or different user forms.

Device 100 includes eight pod structures 101, 102, 103, 104, 105, 106, 107, and 108 that form physically coupled links thereof. Wearable EMG devices employing pod structures (e.g., device 100) are used herein as exemplary wearable EMG device designs, while the present systems, articles, and methods may be applied to wearable EMG devices that do not employ pod structures (or that employ any number of pod structures). Thus, throughout this specification, descriptions relating to pod structures (e.g., functions and/or components of pod structures) should be interpreted as being applicable to any wearable EMG device design, even wearable EMG device designs that do not employ pod structures (except in cases where a pod structure is specifically recited in a claim).

In exemplary device 100 of FIG. 1, each of pod structures 101, 102, 103, 104, 105, 106, 107, and 108 comprises a respective housing having a respective inner volume. Each housing may be formed of substantially rigid material and may be optically opaque. Throughout this specification and the appended claims, the term "rigid" as in, for example, "substantially rigid material," is used to describe a material that has an inherent tendency to maintain its shape and resist malformation/deformation under the moderate stresses and strains typically encountered by a wearable electronic device.

Details of the components contained within the housings (i.e., within the inner volumes of the housings) of pod structures 101, 102, 103, 104, 105, 106, 107, and 108 are not visible in FIG. 1. To facilitate descriptions of exemplary device 100, some internal components are depicted by dashed lines in FIG. 1 to indicate that these components are contained in the inner volume(s) of housings and may not normally be actually visible in the view depicted in FIG. 1, unless a transparent or translucent material is employed to form the housings. For example, any or all of pod structures 101, 102, 103, 104, 105, 106, 107, and/or 108 may include electric circuitry. In FIG. 1, a first pod structure 101 is shown containing electric circuitry 111 (i.e., electric circuitry 111 is contained in the inner volume of the housing of pod structure 101), a second pod structure 102 is shown containing electric circuitry 112, and a third pod structure 108 is shown containing electric circuitry 118. The electric circuitry in any or all pod structures may be communicatively coupled to the electric circuitry in at least one other pod structure by at least one respective communicative pathway (e.g., by at least one electrically conductive pathway and/or by at least one optical pathway). For example, FIG. 1 shows a first set of communicative pathways 121 providing communicative coupling between electric circuitry 118 of pod structure 108 and electric circuitry 111 of pod structure 101, and a second set of communicative pathways 122 providing communicative coupling between electric circuitry 111 of pod structure 101 and electric circuitry 112 of pod structure 102. Communicative coupling between electric circuitries of respective pod structures in device 100 may advantageously include systems, articles, and methods for signal routing as described in U.S. Provisional Patent Application Ser. No. 61/866,960 (now U.S. Non-Provisional patent application Ser. No. 14/461,044) and/or systems, articles, and methods for strain mitigation as described in U.S. Provisional Patent Application Ser. No. 61/857,105 (now U.S. Non-Provisional patent application Ser. No. 14/335,668), both of which are incorporated by reference herein in their entirety.

Throughout this specification and the appended claims the term "communicative" as in "communicative pathway," "communicative coupling," and in variants such as "communicatively coupled," is generally used to refer to an engineered arrangement for transferring and/or exchanging information. Exemplary communicative pathways include, but are not limited to, electrically conductive pathways (e.g., electrically conductive wires, electrically conductive traces), magnetic pathways (e.g., magnetic media), and/or optical pathways (e.g., optical fiber), and exemplary communicative couplings include, but are not limited to, electrical couplings and/or optical couplings.

Each individual pod structure within a wearable EMG device may perform a particular function, or particular functions. For example, in device 100, each of pod structures 101, 102, 103, 104, 105, 106, and 107 includes a respective EMG sensor 110 (only one called out in FIG. 1 to reduce clutter) responsive to (i.e., to in use detect) muscle activity of a user and provide electrical signals in response to the detected muscle activity. Thus, each of pod structures 101, 102, 103, 104, 105, 106, and 107 may be referred to as a respective "sensor pod." Throughout this specification and the appended claims, the term "sensor pod" is used to denote an individual pod structure that includes at least one sensor responsive to (i.e., to in use detect) muscle activity of a user. Each EMG sensor may be, for example, a respective capacitive EMG sensor that detects electrical signals generated by muscle activity through capacitive coupling, such as for example the capacitive EMG sensors described in U.S. Provisional Patent Application Ser. No. 61/771,500 (now U.S. Non-Provisional patent application Ser. No. 14/194,252).

Pod structure 108 of device 100 includes a processor 130 that in use processes the signals provided by the EMG sensors 110 of sensor pods 101, 102, 103, 104, 105, 106, and 107 in response to detected muscle activity. Pod structure 108 may therefore be referred to as a "processor pod." Throughout this specification and the appended claims, the term "processor pod" is used to denote an individual pod structure that includes at least one processor to in use process signals. The processor may be any type of processor, including but not limited to: a digital microprocessor or microcontroller, an application-specific integrated circuit (ASIC), a field-programmable gate array (FPGA), a digital signal processor (DSP), a graphics processing unit (GPU), a programmable gate array (PGA), a programmable logic unit (PLU), or the like, that analyzes the signals to determine at least one output, action, or function based on the signals.

As used throughout this specification and the appended claims, the terms "sensor pod" and "processor pod" are not necessarily exclusive. A single pod structure may satisfy the definitions of both a "sensor pod" and a "processor pod" and may be referred to as either type of pod structure. For greater clarity, the term "sensor pod" is used to refer to any pod structure that includes a sensor and performs at least the function(s) of a sensor pod, and the term processor pod is used to refer to any pod structure that includes a processor and performs at least the function(s) of a processor pod. In device 100, processor pod 108 includes an EMG sensor 110 (not visible in FIG. 1) to sense, measure, transduce or otherwise detect muscle activity of a user, so processor pod 108 could be referred to as a sensor pod. However, in exemplary device 100, processor pod 108 is the only pod structure that includes a processor 130, thus processor pod 108 is the only pod structure in exemplary device 100 that can be referred to as a processor pod. In alternative embodiments of device 100, multiple pod structures may include processors, and thus multiple pod structures may serve as processor pods. Similarly, some pod structures may not include sensors, and/or some sensors and/or processors may be laid out in other configurations that do not involve pod structures.

Processor 130 includes and/or is communicatively coupled to a non-transitory processor-readable storage medium or memory 140. As will be described in more detail later, memory 140 may store, for example, various processor-executable instructions including any or all of: processor-executable EMG processing instructions 141 that, when executed by processor 130, cause processor 130 to process at least one signal provided by at least one EMG sensor 110; first processor-executable communication instructions 142 that, when executed by processor 130, cause processor 130 to communicate with a separate electronic device (not shown in FIG. 1); and/or second processor-executable communication instructions 143 that, when executed by processor 130, cause processor 130 to communicate with a second wearable EMG device (not shown in FIG. 1). For communicating with a separate electronic device and/or a second wearable EMG device, first wearable EMG device 100 includes at least one communication terminal communicatively coupled to processor 130. Throughout this specification and the appended claims, the term "communication terminal" is generally used to refer to any physical structure that provides a telecommunications link through which a data signal may enter and/or leave a device. A communication terminal represents the end (or "terminus") of communicative signal transfer within a device and the beginning of communicative signal transfer with an external device (or external devices). As examples, device 100 includes a first communication terminal 151 and a second communication terminal 152. First communication terminal 151 includes a wireless transmitter and second communication terminal 152 includes a tethered connector port 152. Wireless transmitter 151 may include, for example, a Bluetooth® transmitter (or similar) and connector port 152 may include a Universal Serial Bus port, a mini-Universal Serial Bus port, a micro-Universal Serial Bus port, a SMA port, a THUNDERBOLT® port, or the like.

For some applications, device 100 may also include at least one accelerometer 160 (e.g., an inertial measurement unit, or "IMU," that includes at least one accelerometer and/or at least one gyroscope) responsive to (i.e., to in use detect, sense, or measure) motion effected by a user and provide signals in response to the detected motion. As will be described in more detail later, signals provided by accelerometer 160 may be processed by processor 130 together with signals provided by EMG sensors 110. In such applications, memory 140 may include processor-executable motion processing instructions 144 that, when executed by processor 130, cause processor 130 to process at least one signal provided by at least one accelerometer 160.

Throughout this specification and the appended claims, the term "provide" and variants such as "provided" and "providing" are frequently used in the context of signals. For example, an EMG sensor is described as "providing at least one signal" and an accelerometer is described as "providing at least one signal." Unless the specific context requires otherwise, the term "provide" is used in a most general sense to cover any form of providing a signal, including but not limited to: relaying a signal, outputting a signal, generating a signal, routing a signal, creating a signal, transducing a signal, and so on. For example, a capacitive EMG sensor may include at least one electrode that capacitively couples to electrical signals from muscle activity. This capacitive coupling induces a change in a charge or electrical potential of the at least one electrode which is then relayed through the sensor circuitry and output, or "provided," by the sensor. Thus, the capacitive EMG sensor may "provide" an electrical signal by relaying an electrical signal from a muscle (or muscles) to an output (or outputs). In contrast, an accelerometer may include components (e.g., piezoelectric, piezoresistive, capacitive, etc.) that are used to convert physical motion into electrical signals. The accelerometer may "provide" an electrical signal by detecting motion and generating an electrical signal in response to the motion.

As previously described, each of pod structures 101, 102, 103, 104, 105, 106, 107, and 108 may include electric circuitry (e.g., electrical and/or electronic circuitry). FIG. 1 depicts electric circuitry 111 inside the inner volume of sensor pod 101, electric circuitry 112 inside the inner volume of sensor pod 102, and electric circuitry 118 inside the inner volume of processor pod 108. The electric circuitry in any or all of pod structures 101, 102, 103, 104, 105, 106, 107 and 108 (including electric circuitries 111, 112, and 118) may include any or all of: an amplification circuit to in use amplify electrical signals provided by at least one EMG sensor 110, a filtering circuit to in use remove unwanted signal frequencies from the signals provided by at least one EMG sensor 110, and/or an analog-to-digital conversion circuit to in use convert analog signals into digital signals. Device 100 may also include a battery (not shown in FIG. 1) to provide a portable power source for device 100.

Signals that are provided by EMG sensors 110 in device 100 are routed to processor pod 108 for processing by processor 130. To this end, device 100 employs a set of communicative pathways (e.g., 121 and 122) to route the signals that are output by sensor pods 101, 102, 103, 104, 105, 106, and 107 to processor pod 108. Each respective pod structure 101, 102, 103, 104, 105, 106, 107, and 108 in device 100 is communicatively coupled to, over, or through at least one of the two other pod structures between which the respective pod structure is positioned by at least one respective communicative pathway from the set of communicative pathways. Each communicative pathway (e.g., 121 and 122) may be realized in any communicative form, including but not limited to: electrically conductive wires or cables, ribbon cables, fiber-optic cables, optical/photonic waveguides, electrically conductive traces carried by a rigid printed circuit board, and/or electrically conductive traces carried by a flexible printed circuit board.

The present systems, articles, and methods describe a human-electronics interface in which at least two wearable EMG devices (e.g., a first device 100 and a second device 100) are used to control another electronic device. The human-electronics interface may be characterized as a system that enables electromyographic control of an electronic device.

Figure 2:
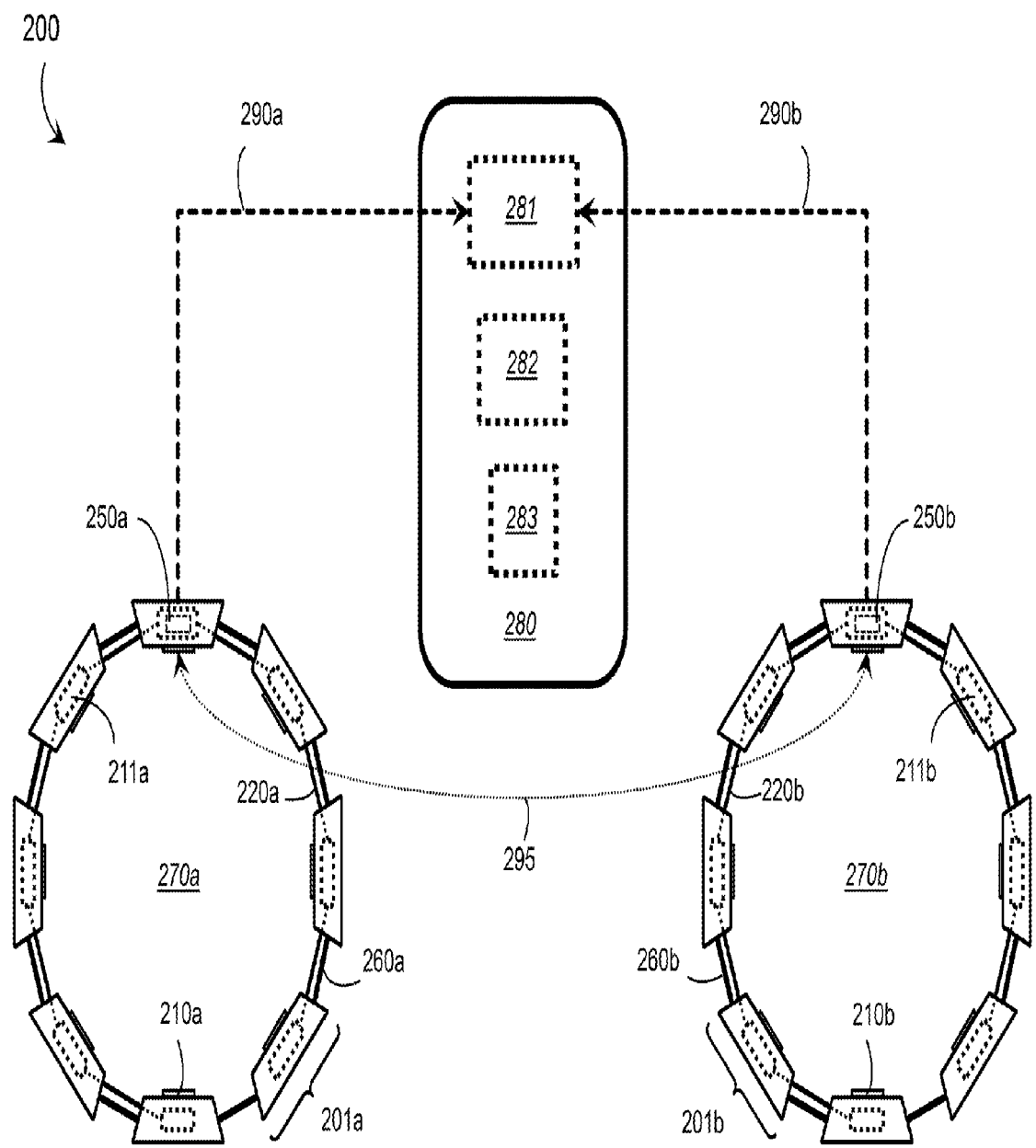
FIG. 2 is an illustrative diagram of a system that enables electromyographic control of an electronic device in accordance with the present systems, articles, and methods.

FIG. 2 is an illustrative diagram of a system 200 that enables electromyographic control of an electronic device in accordance with the present systems, articles, and methods. System 200 includes a first wearable EMG device 270a, a second wearable EMG device 270b, and an electronic device 280, where both the first wearable EMG device 270a and the second wearable EMG device 270b are operable to at least partially control one or more function(s) and/or operation(s) of the electronic device 280. First wearable EMG device 270a and second wearable EMG device 270b may both be substantially similar to wearable EMG device 100 from FIG. 1. That is, wearable EMG device 270a includes a set of pod structures 201a (only one called out in FIG. 2 to reduce clutter) that form physically coupled links of device 270a, where each pod structure 201a includes a respective EMG sensor 210a (e.g., a respective capacitive EMG sensor) responsive to (i.e., to in use sense, measure, transduce or otherwise detect) muscle activity of a user and provide electrical signals in response to the muscle activity. Similarly, wearable EMG device 270b includes a set of pod structures 201b (only one called out in FIG. 2 to reduce clutter) that form physically coupled links of device 270b, where each pod structure 201b includes a respective EMG sensor 210b (e.g., a respective capacitive EMG sensor) responsive to muscle activity of a user and provide electrical signals in response to the muscle activity.

In each device 270a, 270b, each pod structure 201a, 201b is electrically coupled to at least one other pod structure by at least one respective communicative pathway 220a, 220b (respectively) communicatively coupled to route signals in between pod structures (e.g., to in use route signals from sensor pods to a processor pod). Each pod structure 201a, 201b is also physically coupled to two adjacent pod structures by at least one adaptive coupler 260a, 260b (respectively) such that, for each device 270a, 270b, the respective set of pod structures forms a perimeter of a respective annular or closed loop configuration. FIG. 2 shows first device 270a and second device 270b each in a respective expanded annular or closed loop configuration adapted to fit the respective arms of a larger user than the contracted annular or closed loop configuration of device 100 from FIG. 1. As a result, adaptive couplers 260a, 260b (only one called out for each of devices 270a, 270b in FIG. 2) providing adaptive physical coupling between adjacent pairs of pod structures 201a, 201b (respectively) are visible in FIG. 2, whereas such adaptive couplers 260a, 260b are not visible in FIG. 1.

Each pod structure 201a, 201b includes respective electric circuitry 211a, 211b (respectively). At least one electric circuitry 211a, 211b of each of devices 270a and 270b (respectively) may include an IMU and/or at least one accelerometer (e.g., akin to accelerometer 160 in device 100 from FIG. 1; not separately illustrated in FIG. 2). At least one electric circuitry 211a in first device 270a includes a first processor and at least one electric circuitry 211b in second device 270b includes a second processor (e.g., the first and second processors both akin to processor 130 in device 100 of FIG. 1; not separately illustrated in FIG. 2). At least one electric circuitry 211a in first device 270a may include a first non-transitory processor-readable storage medium or memory and at least one electric circuitry 211b in second device 270b may include a second non-transitory processor-readable storage medium or memory (e.g., the first and second memories both akin to memory 140 in device 100 from FIG. 1; not separately illustrated in FIG. 2).

The first memory of first device 270a may store any or all of: processor-executable EMG processing instructions (e.g., instructions 141 in device 100 from FIG. 1; not separately illustrated in FIG. 2) that, when executed by the first processor of first device 270a, cause the first processor to process at least one signal provided by at least one EMG sensor 210a; first processor-executable communication instructions (e.g., instructions 142 in device 100 from FIG. 1; not separately illustrated in FIG. 2) that, when executed by the first processor of first device 270a, cause the first processor to communicate with electronic device 280; second processor-executable communication instructions (e.g., instructions 143 in device 100 from FIG. 1; not separately illustrated in FIG. 2) that, when executed by the first processor of first device 270a, cause the first processor to communicate with second wearable EMG device 270b; and/or processor-executable motion processing instructions (e.g., instructions 144 in device 100 from FIG. 1; not separately illustrated in FIG. 2) that, when executed by the first processor of first device 270a, cause the first processor to process at least one signal provided by at least one accelerometer.

Similarly, the second memory of second device 270b may store any or all of: processor-executable EMG processing instructions (e.g., instructions 141 in device 100 from FIG. 1; not separately illustrated in FIG. 2) that, when executed by the second processor of second device 270b, cause the second processor to process at least one signal provided by at least one EMG sensor 210b; first processor-executable communication instructions (e.g., instructions 142 in device 100 from FIG. 1; not separately illustrated in FIG. 2) that, when executed by the second processor of second device 270b, cause the second processor to communicate with electronic device 280; second processor-executable communication instructions (e.g., instructions 143 in device 100 from FIG. 1; not separately illustrated in FIG. 2) that, when executed by the second processor of second device 270b, cause the second processor to communicate with first wearable EMG device 270a; and/or processor-executable motion processing instructions (e.g., instructions 144 in device 100 from FIG. 1; not separately illustrated in FIG. 2) that, when executed by the second processor of second device 270b, cause the second processor to process at least one signal provided by at least one accelerometer.

First device 270a includes a first communication terminal 250a to in use communicate with electronic device 280 and/or to in use communicate with second device 270b, and similarly second device 270b includes a second communication terminal 250b to in use communicate with electronic device 280 and/or to in use communicate with first device 270a. For example, first device 270a is operative to send communication signals to and/or receive communication signals from electronic device 280 through first communication terminal 250a and/or first device 270a is operative to send communication signals to and/or receive communication signals from second device 270b through first communication terminal 250a. Similarly, second device 270b is operative to send communication signals to and/or receive communication signals from electronic device 280 through second communication terminal 250b and/or second device 270b is operative to send communication signals to and/or receive communication signals from first device 270a through second communication terminal 250b. In some applications, it may be advantageous to include separate communication terminals (e.g., first and second communication terminals) in each of first device 270a and second device 270b, with first device 270a having a first communication terminal 250a to in use communicate with electronic device 280 and a second communication terminal 250a to in use communicate with second device 270b and second device 270b having a first communication terminal 250b to in use communicate with electronic device 280 and a second communication terminal 250b to in use communicate with first device 270a.

Electronic device 280 may be any electronic device, including but not limited to: a computer, a laptop computer, a tablet computer, a mobile phone, a smartphone, a portable electronic device, an audio player, a television, a video player, a video game console, a robot, a light switch, and/or a vehicle. The nature and/or functions of electronic device 280, its operating characteristics and/or the operating characteristics of applications executed by the electronic device 280 may not be a priori known by the first device 270a and/or by second device 270b during use. Electronic device 280 includes a communication terminal (i.e., a third communication terminal) 281 to in use communicate with one or both of first device 270a and/or second device 270b. Device 280 also includes a third processor 282 communicatively coupled to third communication terminal 281 to in use effect functions of electronic device 280 based on communication signals received by third communication terminal 281. Third processor 282 may include or be communicatively coupled to a non-transitory processor-readable storage medium or memory 283 that stores processor-executable instructions which, when executed by third processor 282, cause third processor 282 to effect functions of electronic device 280 (or an application executed by electronic device 280) based on the communication signals received by third communication terminal 281.

In accordance with the present systems, articles, and methods, at least some functions of electronic device 280 may be controlled by first wearable EMG device 270a, at least some functions of electronic device 280 may be controlled by second wearable EMG device 270b, and/or at least some functions of electronic device 280 may be controlled by both first wearable EMG device 270a and second wearable EMG device 270b. In system 200, first wearable EMG device 270a and electronic device 280 are communicatively coupled by first communicative link 290a. More specifically, first communication terminal 250a of first wearable EMG device 270a is communicatively coupled to third communication terminal 281 of electronic device 280 by first communicative link 290a. First communicative link 290a may be used to send communication signals from first wearable EMG device 270a to electronic device 280 and/or to send communication signals from electronic device 280 to first wearable EMG device 270a. First communicative link 290a may be established in a variety of different ways. For example, first communication terminal 250a of first wearable EMG device 270a may include a first tethered connector port (e.g., a USB port, or the like), third communication terminal 281 of electronic device 280 may include a second tethered connector port, and first communicative link 290a may be established through a physical communicative pathway (e.g., an electrical or optical cable, wire, circuit board, or the like) that communicatively couples the first tethered connector port to the second tethered connector port. Alternatively, first communication terminal 250a of first wearable EMG device 270a may include a wireless transmitter (and/or a wireless receiver, e.g., a first wireless transceiver), third communication terminal 281 of electronic device 280 may include a wireless receiver (and/or a wireless transmitter, e.g., a second wireless transceiver) and first communicative link 290a may be representative of wireless communication between first wearable EMG device 270a and electronic device 280 (using, for example, one or more established wireless telecommunication protocol(s), such as Bluetooth®). In some applications, third communication terminal 281 may include a tethered connector port that is communicatively coupled to a wireless receiver (such as a USB dongle communicatively coupled to a tethered connector port of third communication terminal 281). As previously described, first wearable EMG device 270a may include a non-transitory processor-readable storage medium or memory (e.g., memory 140 from FIG. 1) that stores first processor-executable communication instructions (e.g., instructions 142 from FIG. 1) that, when executed by the first processor of first wearable EMG device 270a, cause first wearable EMG device 270a to communicate with electronic device 280 through first communicative link 290a.

Similarly, second wearable EMG device 270b and electronic device 280 are communicatively coupled by second communicative link 290b. More specifically, second communication terminal 250b of second wearable EMG device 270b is communicatively coupled to third communication terminal 281 of electronic device 280 by second communicative link 290b. Second communicative link 290b may be used to send communication signals from second wearable EMG device 270b to electronic device 280 and/or to send communication signals from electronic device 280 to second wearable EMG device 270b. Second communicative link 290b may be established in variety of different ways. For example, second communication terminal 250b of second wearable EMG device 270b may include a first tethered connector port (e.g., a USB port, or the like), third communication terminal 281 of electronic device 280 may include a second tethered connector port, and second communicative link 290b may be established through a physical communicative pathway (e.g., an electrical or optical cable, wire, circuit board, or the like) that communicatively couples the first tethered connector port to the second tethered connector port. Alternatively, second communication terminal 250b of second wearable EMG device 270b may include a wireless transmitter (and/or a wireless receiver, e.g., a third wireless transceiver), third communication terminal 281 of electronic device 280 may include a wireless receiver (and/or a wireless transmitter, e.g., the second wireless transceiver described above) and second communicative link 290b may be representative of wireless communication between second wearable EMG device 270b and electronic device 280 (using, for example, one or more established wireless telecommunication protocol(s), such as Bluetooth®). In some applications, third communication terminal 281 may include a tethered connector port that is communicatively coupled to a wireless receiver (such as a USB dongle communicatively coupled to a tethered connector port of third communication terminal 281). As previously described, second wearable EMG device 270b may include a non-transitory processor-readable storage medium or memory (e.g., memory 140 from FIG. 1) that stores first processor-executable communication instructions (e.g., instructions 142 from FIG. 1) that, when executed by the second processor of second wearable EMG device 270b, cause second wearable EMG device 270b to communicate with electronic device 280 through second communicative link 290b.

Either instead of one of first communicative link 290a and second communicative link 290b, or in addition to both first communicative link 290a and second communicative link 290b, system 200 may include a third communicative link 295 between first wearable EMG device 270a and second wearable EMG device 270b. More specifically, in exemplary system 200, first communication terminal 250a of first wearable EMG device 270a is communicatively coupled to second communication terminal 250b of second wearable EMG device 270b through third communicative link 295. Similar to first communicative link 290a and second communicative link 290b, third communicative link 295 may provide either one-way or two-way signal transfer and may be either wireless or wired. In some applications, it may be advantageous for either or both of first device 270a and/or second device 270b to include multiple communication terminals, with each communication terminal designated for a particular communicative link. For example, first device 270a may include a first communication terminal 250a to communicatively couple to electronic device 280 through first communicative link 290a and a second communication terminal 250a (not separately illustrated in FIG. 2) to communicatively couple to second device 270b through third communicative link 295. Similarly, second device 270b may include a first communication terminal 250b to communicatively couple to electronic device 280 through second communicative link 290b and a second communication terminal 250b (not separately illustrated in FIG. 2) to communicatively couple to first device 270a through third communicative link 295.

As previously described, known proposals for human-electronics interfaces that employ a wearable EMG device are limited because they implement only a single processor-based wearable EMG device that responds to gestures involving only a single part of the user's body. Employing only a single processor-based wearable EMG device unduly restricts the library of gestures available to the user and limits the intuitiveness of the interface itself. In accordance with the present systems, articles, and methods, such limitations may be overcome by a human-electronics interface that employs at least two wearable EMG devices worn at two separate parts/locations of the user's body. The at least two wearable EMG devices may be used to individually control various functions of an electronic device via individually-detected gestures (and individual communicative links to the electronic device, such as first communicative link 290a and second communicative link 290b), or they may be used in combination (e.g., by implementing inter-device communication such as third communicative link 295) to enable more sophisticated and, in some applications, more natural and/or intuitive gestures.

Throughout this specification and the appended claims, reference is often made to multiple (i.e., at least two) wearable EMG devices (such as first wearable EMG device 270a and second wearable EMG device 270b in system 200). Unless the specific context requires otherwise, a first wearable EMG device is characterized as distinct from a second wearable EMG device when all of the following conditions are satisfied:

i. the first wearable EMG device and the second wearable EMG device are physically decoupled from one another (with the possible exception of one or more wired communicative links 295 communicatively coupling between the first and the second wearable EMG devices. In this case, the wired communicative link 295 must be readily detachable from at least one of the first and the second wearable EMG devices by, e.g., removal from a corresponding tethered connector port);

ii. the first wearable EMG device is (or has the capacity to be) worn on a first part/location of the user's body while (i.e., at the same time as) the second wearable EMG device is (or has the capacity to be) worn on a second part/location of the user's body; and iii. the first wearable EMG device comprises a first set of EMG sensors and a first processor, with signals provided by the first set of EMG sensors routed to and processed by the first processor, and the second wearable EMG device comprises a second set of EMG sensors and a second processor, with signals provided by the second set of EMG sensors routed to and processed by the second processor.

Figure 3:
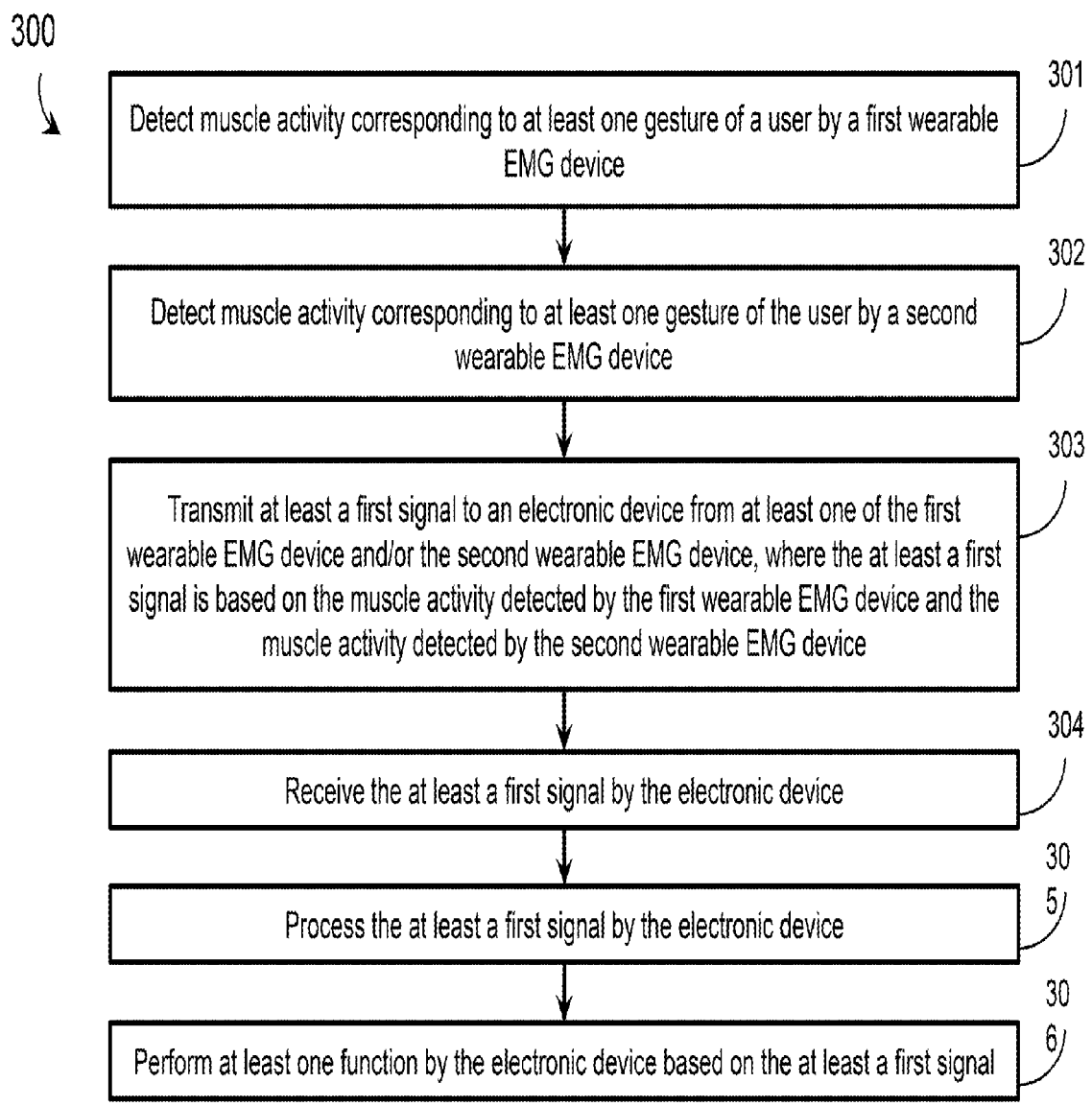
FIG. 3 is a flow-diagram showing a method of using at least one gesture of a user to electromyographically control an electronic device in accordance with the present systems, articles, and methods.

FIG. 3 is a flow-diagram showing a method 300 of using at least one gesture of a user to electromyographically control an electronic device in accordance with the present systems, articles, and methods. The electronic device may be any electronic device (e.g., a processor-based electronic device) as described previously. As will be described in more detail later, "at least one gesture" may include a single gesture that involves multiple parts/locations of a user's body and is simultaneously detected by multiple wearable EMG devices (e.g., one "two-armed" gesture), or multiple gestures that respectively involve different parts/locations of a user's body and are independently detected by multiple respective wearable EMG devices (e.g., two "one-armed" gestures, each using a different arm).

Method 300 may be implemented using a human-electronics interface, such as for example, system 200 from FIG. 2. Throughout the description of method 300 that follows, reference is made to the elements of system 200 from FIG. 2. A person of skill in the art will appreciate that the elements of system 200 are cited in relation to the acts of method 300 as illustrative examples only and that method 300 may be implemented using other human-electronics interfaces.

Method 300 includes six acts 301, 302, 303, 304, 305, and 306, though those of skill in the art will appreciate that in alternative embodiments certain acts may be omitted and/or additional acts may be added. Those of skill in the art will also appreciate that the illustrated order of the acts is shown for exemplary purposes only and may change in alternative embodiments. Acts 301, 302, and 303 are performed at the user-side by wearable EMG devices worn by the user, while acts 304, 305, and 306 are performed at the receiving side by the electronic device being controlled.

At 301, muscle activity corresponding to at least one gesture of a user (i.e., a wearer of at least two wearable EMG devices in accordance with the present systems, articles, and methods) is detected by a first wearable EMG device 270a. As previously described, the muscle activity may be sensed, measured, transduced, or otherwise detected by at least one EMG sensor 210a of the first wearable EMG device 270a and the at least one EMG sensor 210a may provide at least one signal in response to the detected muscle activity. The at least one signal may subsequently be processed by an on-board processor of the first wearable EMG device 270a.

At 302, muscle activity corresponding to at least one gesture of the user is detected by a second wearable EMG device 270b. As previously described, the muscle activity may be sensed, measured, transduced, or otherwise detected by at least one EMG sensor 210b of the second wearable EMG device 270b and the at least one EMG sensor 210b may provide at least one signal in response to the detected muscle activity. The at least one signal may subsequently be processed by an on-board processor of the second wearable EMG device 270b.

The at least one gesture may include a single gesture involving multiple parts/locations of the user's body, such that the at least one gesture detected at 302 may be the same gesture as the at least one gesture detected at 301. In this case, at 301 muscle activity corresponding to a first component of a gesture is detected at a first location of the user's body by the first wearable EMG device 270a and at 302 muscle activity corresponding to a second component of the gesture is detected at a second location of the user's body by the second wearable EMG device 270b. Alternatively, the at least one gesture may include a first gesture involving a first part/location of the user's body and a second gesture involving a second part/location of the user's body, such that the at least one gesture detected at 302 may be a different and/or separate gesture from the at least one gesture detected at 301. In this case, at 301 muscle activity corresponding to a first gesture is detected at a first location of the user's body by the first wearable EMG device 270a and at 302 muscle activity corresponding to a second gesture is detected at a second location of the user's body by the second wearable EMG device 270b.

At 303, at least a first signal is transmitted to the electronic device 280 from at least one of the first wearable EMG device 270a and/or the second wearable EMG device 270b. The at least a first signal is based on the muscle activity detected by the first wearable EMG device 270a at 301 and on the muscle activity detected by the second wearable EMG device 270b at 302. Thus, the at least a first signal may include a result (or results) of on-board processing by respective processors on-board the first and the second wearable EMG devices.

At 304, the at least a first signal is received by the electronic device 280. For example, the at least a first signal may be received by a communication terminal 281 of the electronic device 280, either wirelessly or through a wire connection.

At 305, the at least a first signal is processed by the electronic device 280. For example, the electronic device 280 may include a processor 282 and the at least a first signal may be processed by the processor 282. Processing the at least a first signal by the processor 282 may include determining by the processor 282 (by, for example, executing instructions stored in a memory of the electronic device 280) at least one function or operation of the electronic device 280 (and/or at least one function or operation of an application executed by the electronic device 280) for the electronic device 280 to perform based at least in part on the at least a first signal. Determining a function or operation of the electronic device 280 by the processor 282 may involve, for example, performing a defined mapping or algorithm that produces a mapping.

At 306, the electronic device 280 performs the at least one function or operation determined at 305 based, at least in part, on processing the at least a first signal received at 304. The at least one function or operation performed at 306 depends on the nature of the electronic device 280 and/or on the specific application executed by the electronic device 280. For example, if the electronic device 280 is an audio player (or a computer executing an application that performs audio player functions), then the at least one function or operation may be a PLAY function or operation, a STOP function or operation, a REWIND function or operation, a VOLUME UP function or operation, etc. In accordance with the present systems, articles, and methods, the human-electronics interfaces described herein may be used to control virtually any function(s) or operation(s) of virtually any electronic device.

Depending on the specific implementation, there are various ways in which acts 303, 304, and 305 may be carried out. Some exemplary implementations, all of which may be achieved using system 200 from FIG. 2 and all of which fall within the scope of method 300 from FIG. 3, are now described without limitation.

a Single Gesture Having Separate Components, with Each Component Detected by a Respective Wearable EMG Device and with No Communication Between Wearable EMG Devices In this implementation, a single gesture involves multiple parts/locations of a user's body and a respective wearable EMG device is worn at each part/location of the user's body that is involved in the gesture. In other words, multiple parts/locations of the user's body work together in order to define, perform, complete, or otherwise produce the gesture. For a single gesture having separate components, respective signals detected and transmitted by respective wearable EMG devices are combined or otherwise processed together in order to define the gesture. Thus, the respective components of the gesture are performed at substantially the same time (or within a reasonable amount of time of one another so as not to incur excessive signal processing delays). Examples include: an "arms wide open" gesture with a first wearable EMG device worn on a first arm of the user and a second wearable EMG device worn on a second arm of the user; a "clap hands together" gesture with a first wearable EMG device worn on a first arm of the user and a second wearable EMG device worn on a second arm of the user; a "click heels together" gesture with a first wearable EMG device worn on a first leg of the user and a second wearable EMG device worn on a second leg of the user; etc.

A first component of the gesture is detected by a first wearable EMG device 270a (i.e., at 301) and processed by an on-board processor thereof using, for example, processor-executable EMG processing instructions stored in an on-board memory and executed by the on-board processor of the first wearable EMG device 270a. First processor-executable communication instructions stored in the memory of the first wearable EMG device 270a are executed by the on-board processor of the first wearable EMG device 270a to cause at least a first signal to be transmitted (i.e., at 303) from a communication terminal 250a of the first wearable EMG device 270a to a communication terminal 281 of the electronic device 280 through a first communicative link 290a. The at least a first signal is received by the communication terminal 281 of the electronic device 280 (i.e., at 304).

At substantially the same time, a second component of the gesture is detected by a second wearable EMG device 270b (i.e., at 302) and processed by an on-board processor thereof using, for example, processor-executable EMG processing instructions stored in an on-board memory and executed by the on-board processor of the second wearable EMG device 270b. First processor-executable communication instructions stored in the memory of the second wearable EMG device 270b are executed by the on-board processor of the second wearable EMG device 270b to cause at least a second signal to be transmitted (i.e., at 303) from a communication terminal 250b of the second wearable EMG device 270b to a communication terminal 281 of the electronic device 280 through a second communicative link 290b. The at least a second signal is received by the communication terminal 281 of the electronic device 280 (i.e., at 304). The at least a first signal from the first wearable EMG device 270a and the at least a second signal from the second wearable EMG device 270b are combined or otherwise processed together within the electronic device 280 by a processor 282 therein (i.e., at 305).

A Single Gesture Having Separate Components, with Each Component Detected by a Respective Wearable EMG Device and with Communication Between Wearable EMG Devices In this implementation, the single gesture having separate components may be substantially the same or similar to that described in the previous implementation. A first component of the gesture is detected by a first wearable EMG device 270a (i.e., at 301) and processed by an on-board processor thereof using, for example, processor-executable EMG processing instructions stored in on-board memory and executed by the on-board processor of the first wearable EMG device 270a. First processor-executable communication instructions stored in the memory of the first wearable EMG device 270a are executed by the on-board processor of the first wearable EMG device 270a to cause at least a first signal to be transmitted from a communication terminal 250a of the first wearable EMG device 270a to a communication terminal 250b of a second wearable EMG device 270b through a first communicative link 295. The at least a first signal is received by the communication terminal 250b of the second wearable EMG device 270b. First processor-executable communication instructions stored in the memory of the second wearable EMG device 270b may be executed by the on-board processor of the second wearable EMG device 270b to cause the second wearable EMG device 270b to receive the at least a first signal from the first wearable EMG device 270a.

At substantially the same time, a second component of the gesture is detected by the second wearable EMG device 270b (i.e., at 302) and processed by an on-board processor thereof using, for example, processor-executable EMG processing instructions stored in memory and executed by the on-board processor of the second wearable EMG device 270b to produce at least a second signal. The at least a first signal from the first wearable EMG device 270a and the at least a second signal from the second wearable EMG device 270b may be combined or otherwise processed together by the on-board processor of the second wearable EMG device 270b. Second processor-executable communication instructions stored in an on-board memory of the second wearable EMG device 270b may be executed by the on-board processor of the second wearable EMG device 270b to cause a result of the combination/processing of the at least a first signal and the at least a second signal to be transmitted (i.e., at 303) from the communication terminal 250b of the second wearable EMG device 270b to the electronic device 280 through a communicative link 290b. The result of the combination/processing may be received by the electronic device 280 (i.e., at 304) and further processed by the processor 282 thereof (i.e., at 305).

Alternatively, second processor-executable communication instructions stored in the memory of the second wearable EMG device 270b may be executed by the on-board processor of the second wearable EMG device 270b to cause the at least a first signal from the first wearable EMG device 270a and the at least a second signal from the second wearable EMG device 270b to be transmitted (i.e., at 303) from the communication terminal 250b of the second wearable EMG device 270b to the communication terminal 281 of the electronic device 280 through a second communicative link 290b. The at least a first signal and the at least a second signal may be received by the electronic device 280 (i.e., at 304) and the at least a first signal and the at least a second signal may be combined or otherwise processed by a processor 282 in the electronic device 280 (i.e., at 305).

In some applications, at least one signal may also be sent from the communication terminal 250b of the second wearable EMG device 270b to the communication terminal 250a of the first wearable EMG device 270a through the first communicative link 295 and/or at least one signal may be transmitted (i.e., at 303) from the communication terminal 250a of the first wearable EMG device 270a to the communication terminal 281 of the electronic device 280 through a third communicative link 290a.

Separate Gestures, with Each Gesture Detected by a Respective Wearable EMG Device and with No Communication Between Wearable EMG Devices In this implementation, multiple separate or distinct gestures are performed. Each gesture involves a separate part/location of the user's body and a respective wearable EMG device is worn at each part/location of the user's body that is involved in a gesture. For separate or distinct gestures, respective signals detected and transmitted by respective wearable EMG devices are separately and/or independently processed in order to define multiple gestures. Unlike a single gesture having multiple components, separate gestures may be performed at different times. Examples include: two independent hand or arm gestures, such as "right hand in a first pose, left hand in a second pose" with a first wearable EMG device worn on a first arm of the user and a second wearable EMG device worn on a second arm of the user; two independent foot or leg gestures, such as "right foot in a first pose, left foot in a second pose" with a first wearable EMG device worn on a first leg of the user and a second wearable EMG device worn on a second leg of the user; "right hand in a first pose, right foot in a second pose" with a first wearable EMG device worn on the right arm of the user and a second wearable EMG device worn on the right leg of the user; etc.

A first gesture is detected by a first wearable EMG device 270a (i.e., at 301) and processed by an on-board processor thereof using, for example, processor-executable EMG processing instructions stored in an on-board memory and executed by the on-board processor of the first wearable EMG device 270a. First processor-executable communication instructions stored in the memory of the first wearable EMG device 270a are executed by the on-board processor of the first wearable EMG device 270a to cause at least a first signal to be transmitted (i.e., at 303) from a communication terminal 250a of the first wearable EMG device 270a to a communication terminal 281 of the electronic device 280 through a first communicative link 290a. The at least a first signal is received by the communication terminal 281 of the electronic device 280 (i.e., at 304).

Substantially independently of the first gesture (including with respect to time, meaning there may or may not be a complete or a partial overlap in time), a second gesture is detected by a second wearable EMG device 270b (i.e., at 302) and processed by an on-board processor thereof using, for example, processor-executable EMG processing instructions stored in an on-board memory and executed by the on-board processor of the second wearable EMG device 270b. First processor-executable communication instructions stored in the memory of the second wearable EMG device 270b are executed by the on-board processor of the second wearable EMG device 270b to cause at least a second signal to be transmitted (i.e., at 303) from a communication terminal 250b of the second wearable EMG device 270b to a communication terminal 281 of the electronic device 280 through a second communicative link 290b. The at least a second signal is received by the communication terminal 281 of the electronic device 280 (i.e., at 304). The at least a first signal from the first wearable EMG device 270a and the at least a second signal from the second wearable EMG device 270b are processed substantially independently of one another within the electronic device 280 by a processor 282 therein (i.e., at 305).

Separate Gestures, with Each Gesture Detected by a Respective Wearable EMG Device and with Communication Between Wearable EMG Devices In this implementation, the separate gestures may be substantially the same or similar to those described in the previous implementation. A first gesture is detected by a first wearable EMG device 270a (i.e., at 301) and processed by an on-board processor thereof using, for example, processor-executable EMG processing instructions stored in an on-board memory and executed by the on-board processor of the first wearable EMG device 270a. First processor-executable communication instructions stored in the memory of the first wearable EMG device 270a are executed by the on-board processor of the first wearable EMG device 270a to cause at least a first signal to be transmitted from a communication terminal 250a of the first wearable EMG device 270a to a communication terminal 250b of a second wearable EMG device 270b through a first communicative link 295. The at least a first signal is received by the communication terminal 250b of the second wearable EMG device 270b. First processor-executable communication instructions stored in a memory of the second wearable EMG device 270b are executed by the on-board processor of the second wearable EMG device 270b to cause the second wearable EMG device 270b to receive the at least a first signal from the first wearable EMG device 270a. The at least a first signal is then transmitted (i.e., at 303) from the communication terminal 250b of the second wearable EMG device 270b to the communication terminal 281 of the electronic device 280 through another communicative link 290b; received by the electronic device 280 (i.e., at 304); and processed by the electronic device 280 (i.e., at 305). In this way, the second wearable EMG device 270b is used to route signals from the first wearable EMG device 270a to the electronic device 280.

Substantially independently of the first gesture (including with respect to time), a second gesture is detected by the second wearable EMG device 270b (i.e., at 302) and processed by an on-board processor thereof using, for example, processor-executable EMG processing instructions stored in an and the on-board memory and executed by the on-board processor of the second wearable EMG device 270b to produce at least a second signal. Second processor-executable communication instructions stored in the memory of the second wearable EMG device 270b may be executed by the on-board processor of the second wearable EMG device 270b to cause the at least a second signal to be transmitted (i.e., at 303) from the communication terminal 250b of the second wearable EMG device 270b to the electronic device 280 through communicative link 290b. The at least a second signal may be received by the electronic device 280 (i.e., at 304) and further processed by the processor 282 thereof (i.e., at 305).

In some applications, at least one signal may also be sent from the communication terminal 250b of the second wearable EMG device 270b to the communication terminal 250a of the first wearable EMG device 270a through the first communicative link 295 and/or at least one signal may be transmitted (i.e., at 303) from the communication terminal 250a of the first wearable EMG device 270a to the communication terminal 281 of the electronic device 280 through a third communicative link 290a.

As previously described, in some applications it may be advantageous to combine EMG signals with motion signals sensed, measured or otherwise detected, for example, by an accelerometer. To this end, any or all of the wearable EMG devices described herein may include at least one accelerometer, and method 300 may further include detecting motion corresponding to at least one gesture of the user by the first wearable EMG device such that the at least a first signal transmitted by the first wearable EMG device (e.g., at 303) is based at least in part on the motion detected by the first wearable EMG device, and/or detecting motion corresponding to at least one gesture of the user by the second wearable EMG device such that the at least a second signal transmitted by the second wearable EMG device (e.g., at 303) is based at least in part on the motion detected by the second wearable EMG device.

As previously described, acts 301, 302, and 303 of method 300 are performed at the user-side by wearable EMG devices worn by the user, while acts 304, 305, and 306 are performed at the receiving side by the electronic device being controlled. For this reason, method 300 may be treated, in some cases, as two separate methods: a first method of producing and transmitting EMG-based control signals comprising acts 301, 302, and 303, and a second method of receiving and responding to EMG-based control signals comprising acts 304, 305, and 306.

The various embodiments described herein provide systems, articles, and methods for human-electronics interfaces that enhance user experience by enabling a user to perform a wider variety of more natural and intuitive gestures. Known proposals for EMG-based human-electronics interfaces employ a single processor-based wearable EMG device (worn, for example, on one arm of the user) and thereby constrain the user to one-sided, asymmetric gestures. Users naturally and intuitively want to use multiple parts/locations of their body in a human-electronics interface (e.g., use both arms/hands to manipulate a projection of a three dimensional model), and the present systems, articles, and methods enable such by providing human-electronics interfaces that employ multiple wearable EMG devices.

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect," to, at least, provide," "to, at least, transmit," and so on.

Furthermore, throughout this specification and the appended claims the terms "first," "second," "third," etc., are often used to distinguish between separate ones of the same or similar type of element. Examples include, without limitation: "a first communication terminal," "a second communication terminal," "a third communication terminal," etc. In such instances, the terms "first," "second," "third," etc. are used strictly for the purpose of distinguishing like elements and are in no way indicative of priority, sequence, or importance. The assignment of the terms "first," "second," "third," etc. is arbitrary and may change between specific descriptions, such that an element that is identified as a "first" element in one description (i.e., a description of one particular example) may be identified as a "second" element in another description (i.e., a description of another particular example).

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other portable and/or wearable electronic devices, not necessarily the exemplary wearable electronic devices generally described above.

For instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs executed by one or more computers (e.g., as one or more programs running on one or more computer systems), as one or more programs executed by on one or more controllers (e.g., microcontrollers) as one or more programs executed by one or more processors (e.g., microprocessors), as firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any processor-readable medium for use by or in connection with any processor-related system or method. In the context of this disclosure, a memory is a processor-readable medium that is an electronic, magnetic, optical, or other physical device or means that contains or stores a computer and/or processor program. Logic and/or the information can be embodied in any processor-readable medium for use by or in connection with an instruction execution system, apparatus, or device, such as a processor-based system, processor-containing system, or other system that can fetch the instructions from the instruction execution system, apparatus, or device and execute the instructions associated with logic and/or information.

In the context of this specification, a "non-transitory processor-readable medium" can be any element that can store the program associated with logic and/or information for use by or in connection with the instruction execution system, apparatus, and/or device. The processor-readable medium can be, for example, but is not limited to, an electronic, magnetic, optical, electromagnetic, infrared, or semiconductor system, apparatus or device. More specific examples (a non-exhaustive list) of the processor-readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other non-transitory media.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to: U.S. Provisional Patent Application Ser. No. 61/874,846; US Provisional Patent Application Ser. No. 61/857,105 (now U.S. Non-Provisional patent application Ser. No. 14/335,668); U.S. Provisional Patent Application Ser. No. 61/752,226 (now U.S. Non-Provisional patent application Ser. No. 14/155,107); U.S. Provisional Patent Application Ser. No. 61/768,322 (now U.S. Non-Provisional patent application Ser. No. 14/186,889); U.S. Provisional Patent Application Ser. No. 61/771,500 (now U.S. Non-Provisional patent application Ser. No. 14/194,252); U.S. Provisional Application Ser. No. 61/860,063 (now U.S. Non-Provisional patent application Ser. No. 14/276,575), U.S. Provisional Application Ser. No. 61/866,960 (now U.S. Non-Provisional patent application Ser. No. 14/461,044), U.S. Provisional Patent Application Ser. No. 61/869,526 (now U.S. Non-Provisional patent application Ser. No. 14/465,194), and U.S. Provisional Patent Application Ser. No. 61/872,569, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A first wearable electromyography ("EMG") device to be worn on a first arm of a user and for use in conjunction with a second wearable EMG device worn on a second arm of the user to enable the user to control an electronic device with a two-arm gesture, the first wearable EMG device comprising:

at least one EMG sensor responsive to muscle activity in a first arm of the user and to provide at least one signal in response to a detected muscle activity in the first arm of the user;

a processor communicatively coupled to the at least one EMG sensor, the processor to process the at least one signal provided by the at least one EMG sensor;

at least one communication terminal communicatively coupled to the processor to send communication signals to both the electronic device and the second wearable EMG device and to receive communication signals from at least the second wearable EMG device, the communication signals received from the second wearable EMG device indicative of muscle activity in the second arm of the user detected by the second EMG device and the communication signals sent to the electronic device indicative of both muscle activity in the first arm of the user and muscle activity in the second arm of the user; and a non-transitory processor-readable storage medium communicatively coupled to the processor, wherein the non-transitory processor-readable storage medium stores:

processor-executable EMG processing instructions that, when executed by the processor, cause the processor to process the at least one signal provided by the at least one EMG sensor, first processor-executable communication instructions that, when executed by the processor, cause the processor to communicate with the electronic device, and second processor-executable communication instructions that, when executed by the processor, cause the processor to communicate with the second wearable EMG device.

2. The first wearable EMG device of claim 1, further comprising:

at least one accelerometer communicatively coupled to the processor, the at least one accelerometer responsive to motion effected by the first arm of the user and to provide at least one signal in response to a detected motion of the first arm of the user, and wherein the non-transitory processor-readable storage medium further stores processor-executable motion processing instructions that, when executed by the processor, cause the processor to process the at least one signal provided by the at least one accelerometer.

3. The first wearable EMG device of claim 1, wherein the at least one communication terminal includes at least one of a wireless communication terminal and a tethered connector port.

4. The first wearable EMG device of claim 1, wherein the at least one communication terminal includes a first communication terminal communicatively coupled to send communication signals to the electronic device, and a second communication terminal communicatively coupled to send communication signals to the second wearable EMG device and receive communication signals from the second wearable EMG device.

5. A system that enables electromyographic control of an electronic device via a two-arm gesture performed by a user, the system comprising:

a first wearable EMG device comprising:

at least a first EMG sensor responsive to muscle activity in a first arm of the user and provide at least one signal in response to a detected muscle activity in the first arm of the user, a first processor communicatively coupled to the at least a first EMG sensor, the first processor to process the at least one signal provided by the at least a first EMG sensor, a first non-transitory processor-readable storage medium communicatively coupled to the first processor, wherein the first non-transitory processor-readable storage medium stores first processor-executable EMG processing instructions that, when executed by the first processor, cause the first processor to process at least one signal provided by the at least a first EMG sensor, and a first communication terminal communicatively coupled to the first processor, the first communication terminal communicatively coupled to transmit communication signals from the first wearable EMG device;

a second wearable EMG device comprising:

at least a second EMG sensor responsive to detect muscle activity in the second arm of the user and provide at least one signal in response to a detected muscle activity in the second arm of the user, a second processor communicatively coupled to the at least a second EMG sensor, the second processor to process the at least one signal provided by the at least a second EMG sensor, a second non-transitory processor-readable storage medium communicatively coupled to the second processor, wherein the second non-transitory processor-readable storage medium stores second processor-executable EMG processing instructions that, when executed by the second processor, cause the second processor to process at least one signal provided by the at least a second EMG sensor, and a second communication terminal communicatively coupled to the second processor, the second communication terminal communicatively coupled to transmit communication signals from the second wearable EMG device;

and an electronic device comprising:

a third communication terminal communicatively coupled to receive communication signals from at least one of the first wearable EMG device and the second wearable EMG device, a third processor communicatively coupled to the third communication terminal, the third processor to effect functions of the electronic device based on the communication signals received by the third communication terminal, and a third non-transitory processor-readable storage medium communicatively coupled to the third processor, wherein the third non-transitory processor-readable storage medium stores processor-executable instructions that, when executed by the third processor, cause the third processor to effect functions of the electronic device based at least in part on the communication signals received by the third communication terminal.

6. The system of claim 5, wherein at least one of the first communication terminal of the first wearable EMG device and the second communication terminal of the second wearable EMG device is receptive of communication signals from the other one of the second communication terminal of the second wearable EMG device and the first communication terminal of the first wearable EMG device.

7. The system of claim 6, wherein:

the first non-transitory processor-readable storage medium communicatively coupled to the first processor of the first wearable EMG device further stores first processor-executable communication instructions that, when executed by the first processor, cause the first processor to communicate with the second wearable EMG device; and the second non-transitory processor-readable storage medium communicatively coupled to the second processor of the second wearable EMG device further stores second processor-executable communication instructions that, when executed by the second processor, cause the second processor to communicate with the first wearable EMG device.

8. The system of claim 5, wherein:

the first wearable EMG device further comprises at least a first accelerometer communicatively coupled to the first processor, the at least a first accelerometer responsive to motion effected by the first arm of the user and provide at least one signal in response to a detected motion; and the second wearable EMG device further comprises at least a second accelerometer communicatively coupled to the second processor, the at least a second accelerometer responsive to motion effected by the second arm of the user and provide at least one signal in response to a detected motion.

9. The system of claim 8, wherein:

the first non-transitory processor-readable storage medium communicatively coupled to the first processor of the first wearable EMG device further stores first processor-executable motion instructions that, when executed by the first processor, cause the first processor to process the at least one signal provided by the at least a first accelerometer; and the second non-transitory processor-readable storage medium communicatively coupled to the second processor of the second wearable EMG device further stores second processor-executable motion instructions that, when executed by the second processor, cause the second processor to process the at least one signal provided by the at least a second accelerometer.

10. The system of claim 5, wherein the first communication terminal, the second communication terminal, and the third communication terminal each comprises a respective wireless communication terminal.

11. The system of claim 5, wherein the electronic device is selected from a group consisting of: a computer, a laptop computer, a tablet computer, a mobile phone, a smartphone, a portable electronic device, an audio player, a television, a video player, a video game console, a robot, a light switch, and a vehicle.

12. A method of using a two-arm gesture of a user to electromyographically control an electronic device, the method comprising:

detecting muscle activity in a first arm of the user by a first wearable EMG device, the muscle activity in the first arm of the user corresponding to a first component of the two-arm gesture;

detecting muscle activity in a second arm of the user by a second wearable EMG device, the muscle activity in the second arm of the user corresponding to a second component of the two-arm gesture;

transmitting at least a first signal to the electronic device from at least the first wearable EMG device, wherein the at least a first signal is based at least in part on the muscle activity detected in the first arm of the user by the first wearable EMG device and the muscle activity detected in the second arm of the user by the second wearable EMG device;

receiving the at least a first signal by the electronic device;

processing the at least a first signal by the electronic device; and performing at least one function by the electronic device based at least in part on the processing the at least a first signal.

13. The method of claim 12, wherein the first wearable EMG device is worn on a first arm of the user and the second wearable EMG device is worn on a second arm of the user.

14. The method of claim 12, wherein transmitting at least a first signal to the electronic device from at least the first wearable EMG device includes transmitting a first signal to the electronic device from the first wearable EMG device and transmitting a second signal to the electronic device from the second wearable EMG device, and wherein the first signal is based at least in part on the muscle activity detected by the first wearable EMG device and the second signal is based at least in part on the muscle activity detected by the second wearable EMG device.

15. The method of claim 12, wherein transmitting at least a first signal to the electronic device from at least the first wearable EMG device includes transmitting a first signal from the first wearable EMG device to the second wearable EMG device and transmitting at least a second signal from the second wearable EMG device to the electronic device, and wherein the first signal is based at least in part on the muscle activity detected by the first wearable EMG device and the at least a second signal is based at least in part on both the muscle activity detected by the first wearable EMG device and the muscle activity detected by the second wearable EMG device.

16. The method of claim 12, further comprising:

transmitting at least a second signal from the first wearable EMG device to the second wearable EMG device.

17. The method of claim 16, further comprising:

transmitting at least a third signal from the second wearable EMG device to either the first wearable EMG device or the electronic device.

18. The method of claim 12, further comprising:

detecting motion corresponding to the two-arm gesture of the user by the first wearable EMG device, wherein the at least a first signal is based at least in part on the motion detected by the first wearable EMG device.

19. The method of claim 18, further comprising:

detecting motion corresponding to the two-arm gesture of the user by the second wearable EMG device, wherein the at least a first signal is based at least in part on the motion detected by the second wearable EMG device.

* * * * *